US00PP28143P3

(12) United States Plant Patent
Van Swieten

(10) Patent No.: US PP28,143 P3
(45) Date of Patent: Jun. 27, 2017

(54) ***PHALAENOPSIS* ORCHID PLANT NAMED 'PHALDESAL'**

(50) Latin Name: ***Phalaenopsis* hybrid**
Varietal Denomination: Phaldesal

(71) Applicant: ANTHURA B.V., Bleiswijk (NL)

(72) Inventor: Martinus Nicolaas Gerardus Van Swieten, Leimuiden (NL)

(73) Assignee: ANTHURA B.V., Bleiswijk (NL)

( * ) Notice: Subject to any disclaimer, the term of this patent is extended or adjusted under 35 U.S.C. 154(b) by 48 days.

(21) Appl. No.: 14/545,826

(22) Filed: Jun. 24, 2015

(65) Prior Publication Data

US 2016/0381854 P1 Dec. 29, 2016

(51) Int. Cl.
*A01H 5/02* (2006.01)

(52) U.S. Cl.
USPC ..... Plt./311

(58) Field of Classification Search
USPC ..... Plt./311
See application file for complete search history.

*Primary Examiner* — Keith Robinson

(74) *Attorney, Agent, or Firm* — Jondle & Associates, P.C.

(57) ABSTRACT

A new and distinct variety of *Phalaenopsis* plant named 'PHALDESAL', particularly characterized by having white flecked flowers, 2 to 5 peduncles, a peduncle that is long and moderate, leaves that are narrow oblong and moderately elongated, and is propagated by tissue culture is disclosed.

3 Drawing Sheets

Genus and species: *Phalaenopsis* hybrid.
Variety denomination: 'PHALDESAL'.

BACKGROUND OF THE NEW PLANT

The present invention comprises a new and distinct cultivar of *Phalaenopsis* plant, botanically known as *Phalaenopsis* of the Orchidaceae family, and hereinafter referred to by the cultivar name 'PHALDESAL'.

*Phalaenopsis* comprises a genus of about 60 species of herbaceous perennials many of which, or the hybrids thereof, are suitable for cultivar in the home or greenhouse. *Phalaenopsis* is predominantly epiphytic or rock dwelling, and is native to tropical Asia, the Malay Archipelago, and Oceania. The species typically has 2-ranked, fleshy, oblong or elliptic leaves affixed to a short central stem (monopodial growth), which vary in size from 12 to 20 cm to over 60 cm. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes or panicles, often with many showy flowers which open in succession beginning with the lowermost. The flowers possess three sepals and three petals; the lateral ones being alike. The lowermost petals, called the labellum, are three-lobed and are often more brightly-colored than the other flower segments. Flower colors include various shades of pink, white, yellow, and red-brown.

*Phalaenopsis* orchids are typically propagated from seeds. Asexual propagation of *Phalaenopsis* is often done from off-shoots which arise from the lower bracts of the inflorescence. The resulting plants are detached from the mother plants and may be planted in a suitable substrate.

The new *Phalaenopsis* 'PHALDESAL' is particularly characterized by its attractive and unique white flecked flowers, economical propagation by tissue culture, rapid growth, and a plant dimension suitable for packaging and shipping to the market.

'PHALDESAL' is a product of a planned breeding program conducted by the inventor in Bleiswijk, The Netherlands.

The new *Phalaenopsis* 'PHALDESAL' originated from a cross made in August 2005 in Bleiswijk, The Netherlands. The female parent is a white flecked *Phalaenopsis* pot plant named '01-1758' (unpatented), while the male parent is a white *Phalaenopsis* pot plant named '06285-0001' (unpatented). A single plant was selected in August 2008 and has been asexually reproduced repeatedly by meristem tissue culture in Bleiswijk, The Netherlands over a 3-year period. The new variety has been found to retain its distinctive characteristics through successive asexual propagations.

Asexual reproduction of 'PHALDESAL' by tissue culture was first performed in December 2011 in Bleiswijk, The Netherlands and has demonstrated that the new cultivar is firmly fixed and retained through successive generations of asexual reproduction.

Plant Breeder's Rights for this variety have not been applied for. 'PHALDESAL' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands.

1) White flecked flowers, the intensity of the flecks depends on the temperature during opening of the flower buds;
2) 2 to 5 peduncles;
3) Peduncle is long and moderate;

4) The shape of the leaf is narrow oblong and moderately elongated; and
5) Plants are propagated by meristem tissue culture.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs are of a 50-week old plant grown in a greenhouse in Bleiswijk, The Netherlands in March 2015.

DESCRIPTION OF THE NEW VARIETY

Figure 1:
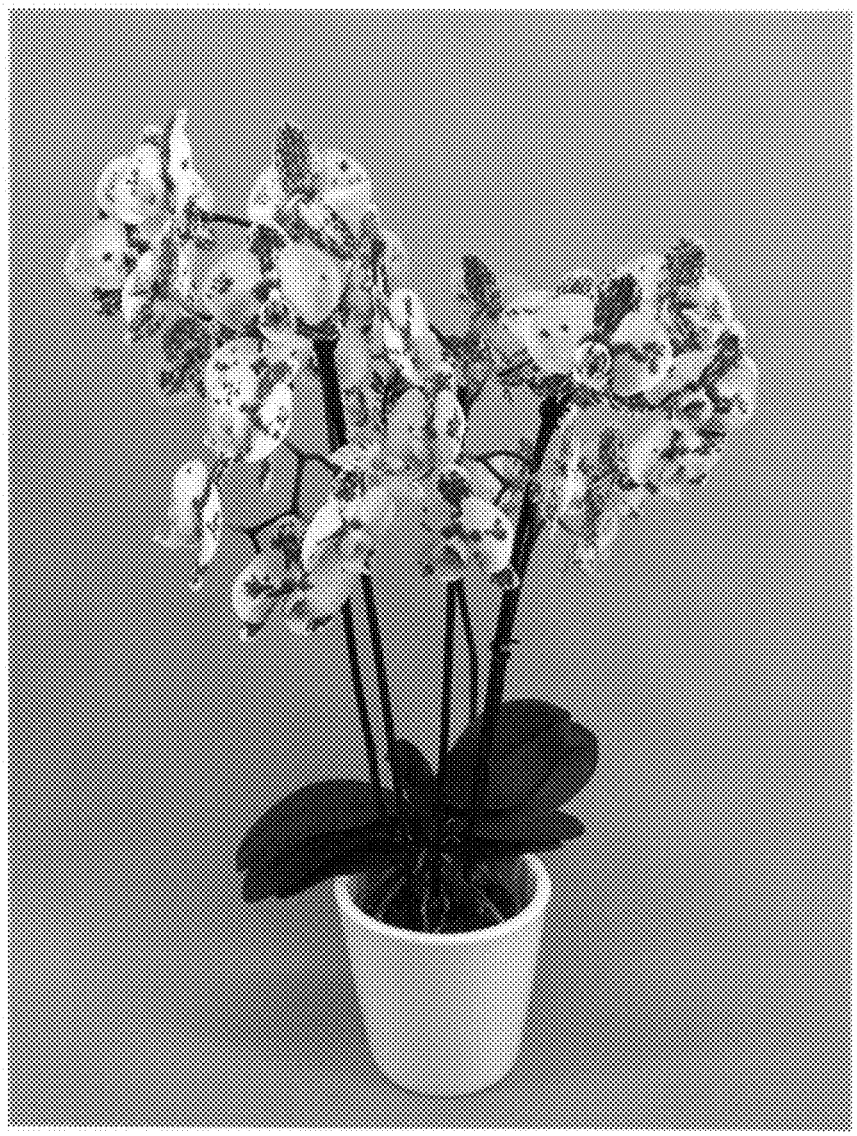
FIG. 1 shows the overall plant habit, including blooms and foliage of 'PHALDESAL'.
Figure 2:
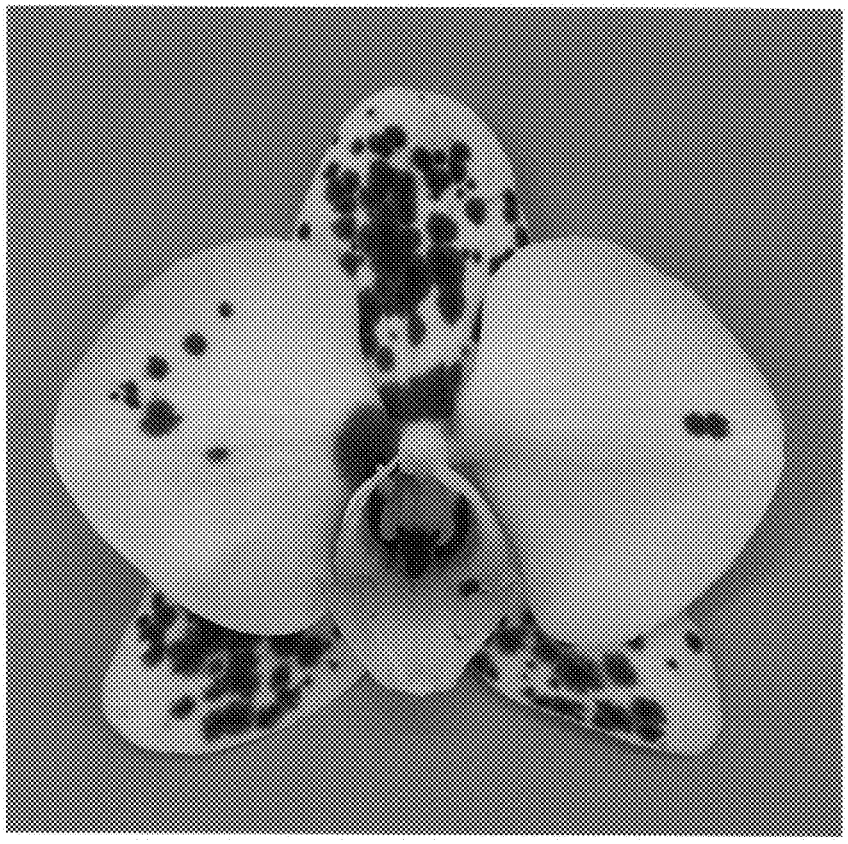
FIG. 2 shows a close-up of a flower of 'PHALDESAL'.
Figure 3:
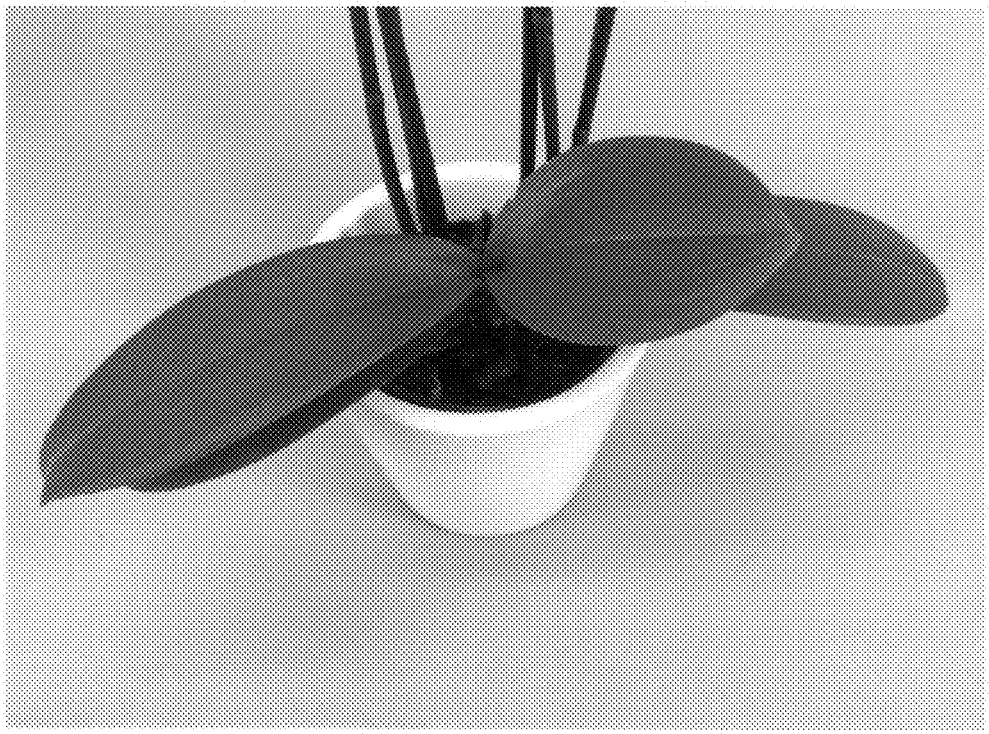
FIG. 3 shows a close-up of the leaves of 'PHALDESAL'.

The following detailed description sets forth the distinctive characteristics of 'PHALDESAL'. The data which define these characteristics were collected from asexual reproductions carried out in Bleiswijk, The Netherlands. The plant history was taken on 50-week old plants which were planted from a nursery tray in 12 centimeter pots and grown in a greenhouse between 27° C. to 29° C. for 30 weeks, continued by a cooling period of 8 weeks between 18° C. to 20° C. and 12 weeks in a greenhouse of 21° C. Observations were made in March 2015. Color readings were taken under 4-6000 lux natural light in the greenhouse. Color references are primarily to The R.H.S. Colour Chart of The Royal Horticultural Society of London (R.H.S.) (2001).

DETAILED BOTANICAL DESCRIPTION

Classification:
- *Family*.—Orchidaceae.
- *Botanical*.—*Phalaenopsis* Hybrid.
- *Common name*.—Moth Orchid.
- *Variety name*.—'PHALDESAL'.

Parentage:
- *Female parent*.—*Phalaenopsis* cultivar '01-1758' (unpatented).
- *Male parent*.—*Phalaenopsis* cultivar '06285-0001' (unpatented).

Propagation:
- *Type*.—Tissue culture.

Plant:
- *Crop time* (*time to produce a finished flowering plant*).—48 to 50 weeks for a 12 cm pot.
- *Growth habit of peduncle*.—Standard, green leaves, panicle.
- *Height* (*including pot, including inflorescence*).—55.0 cm to 65.0 cm.
- *Width* (*measured from leaf tips*).—25.0 cm to 30.0 cm.
- *Vigor*.—Moderate.

Roots:
- *Root description*.—Greyed-green-colored roots (RHS 190B/C) with lightly branching lateral roots having green colored root tips (RHS 144A).

Leaves:
- *Mature leaves*.—Quantity per plant: 6 to 8 leaves are produced before flowering. Length (fully expanded): 15.0 cm to 19.0 cm. Width: 6.0 cm to 7.0 cm. Position of broadest part of leaf: At the middle. Shape: Narrow oblong. Base shape: Moderately elongated. Apex: Unequal acute. Leaf blade angle with the petiole: Between 0 degrees and 30 degrees (measured from the horizontal position). Leaf margin: Entire. Color: Upper surface: RHS 146A. Lower surface: RHS 146B. Variegation: Absent. Texture: Upper surface: A little bit rough. Lower surface: Smooth. Thickness: 2.6 mm to 2.9 mm. Venation: Pattern: Parallel. Color of the midvein: Upper surface: RHS 146A. Lower surface: RHS 146B.

Peduncle:
- *Quantity per plant*.—2 to 5.
- *Number of flowers per peduncle*.—6 to 10.
- *Length*.—45.0 cm to 55.0 cm.
- *Diameter*.—5.4 mm to 5.8 mm.
- *Strength*.—Moderate.
- *Aspect*.—Upright.
- *Texture*.—Smooth.
- *Color*.—Brown-green (RHS 200A, 201A and 191A).
- *Internode length*.—45.0 mm to 55.0 mm.
- *Callosities*.—None.

Inflorescence description:
- *Appearance*.—Upright to slightly pendant, panicle inflorescence with bilaterally symmetrical flowers that open in succession beginning with the lowermost flower.
- *Inflorescence size*.—Height (from base to tip): 170.0 mm to 220.0 mm. Diameter: 4.2 mm to 4.4 mm.
- *Number of inflorescences on plant*.—2 to 5.
- *Flowering time*.—First flowers can be expected 10 to 11 months after planting in a 12 cm pot.
- *Flower*.—Height: 78.0 mm to 83.0 mm. Diameter: 78.0 mm to 83.0 mm. Depth of lip: 19.0 mm to 21.0 mm.
- *Flower longevity*.—On the plant: 11 to 13 weeks.
- *Flower shape*.—Flat.
- *Fragrance*.—Absent.
- *Petals*.—Arrangement: Open. Shape: Semi-circular. Apex: Mucronate and symmetric. Margin: Entire. Length (from base to tip): 35.0 mm to 38.0 mm. Width: 45.0 mm to 47.0 mm. Position of broadest part of petal: At the middle. Color (when fully opened): Main color: White (RHS 155C) flecked (RHS 71A, 78A). At the base: White (RHS 155C). Netting of the petals: None.
- *Dorsal sepal*.—Shape: Elliptic. Margin: Entire. Length (from base to tip): 39.0 mm to 41.0 mm. Width: 29.0 mm to 31.0 mm. Position of broadest part of dorsal sepal: At the middle. Color (when fully opened): Dorsal sepal is more flecked than the petals. Main color: White (RHS 155C) flecked (RHS 71A, 78A). At the base: White (RHS 155C). Netting of the dorsal sepal: None.
- *Lateral sepals*.—Shape: Ovate. Margin: Entire. Length (from base to tip): 43.0 mm to 45.0 mm. Width: 24.0 mm to 26.0 mm. Position of broadest part of lateral sepal: At the middle. Color (when fully opened): Lateral sepals are more flecked than the petals. Main color: White (RHS 155C) flecked (RHS 71A, 78A). At the base: White (RHS 155C). Netting of the lateral sepal: None.
- *Labellum* (*lip*).—Margin: Entire. Shape: Triangular. Length: 20.0 mm to 22.0 mm. Width: 23.0 mm to 25.0 mm. Whiskers: Present. Length of whiskers: Very long.

*Lateral lobe*.—Shape: Type V (as described in the International Union for the Protection of New Varieties of Plants (UPOV) Test Guidelines for *Phalaenopsis*). Color: White (RHS 155C) and yellow (RHS 7A, 1A) with dark purple stripe towards the callus (RHS 59A). Netting of the lateral lobe: None.

*Apical lobe*.—Shape: Triangular-trullate. Length: 21.0 mm to 23.0 mm. Width: 22.0 mm to 24.0 mm. Netting of the apical lobe: None. Color: White (RHS 155C) and yellow-green towards the callus (RHS 1A, 3A).

*Callus*.—Color: Dark brown (RHS 200B).

Reproductive organs:

*Arrangement*.—The stamens, style and stigmas are fused into a single, short structure called the column, possessing one terminal anther with pollen grains united into pollinia, which are covered by an anther cap. The stigma is located under the column behind the pollinia. The ovary is inferior with three carpels present.

*Column*.—Length: 9.0 mm to 10.0 mm. Diameter: 4.5 mm to 5.5 mm. Color: White (RHS 155C) and purple towards the bottom (RHS 71A, 78A).

*Pollinia*.—Quantity: 2. Size: 9.0 mm to 10.0 mm. Color: Yellow-orange (RHS 23A).

*Ovary*.—Length: Not visible. Diameter: 2.4 mm to 2.6 mm.

*Pedicel*.—Length: 28.0 mm to 31.0 mm. Diameter: 3.2 mm to 3.4 mm. Texture: Smooth. Color: Green (RHS 146C) at the base and light green (RHS 145D) towards the flower.

Disease, pest, and stress resistance: No specific resistance or susceptibility observed.

Temperature tolerance: Tolerant to a low temperature of 15° C. and a high temperature about 30° C.

COMPARISON WITH PARENTAL AND COMMERCIAL VARIETIES

The female parent of 'PHALDESAL', cultivar '01-1758' (unpatented), is no longer in existence, so a meaningful comparison cannot be made.

'PHALDESAL' differs from male parent '06285-0001' (unpatented) in that 'PHALDESAL' has white flecked flowers and a dark brown callus, whereas '06285-0001' has white flowers and a yellow dotted callus. Additionally, 'PHALDESAL' has a smaller flower diameter than '06285-0001'.

'PHALDESAL' differs from commercial variety 'PHALCASWOJ' (unpatented) in that 'PHALDESAL' has long whiskers and an apical lobe of the lip that is white with yellow-green towards the callus, whereas 'PHALCASWOJ' has short whiskers and an apical lobe of the lip that is greyed-orange and greyed-purple with white towards the whiskers. Additionally, 'PHALDESAL' has flowers with lighter flecks than 'PHALCASWOJ'.

I claim:

1. A new and distinct variety of *Phalaenopsis* plant named 'PHALDESAL', substantially as described and illustrated herein.

* * * * *